(12) United States Patent
Di Palo et al.

(10) Patent No.: US 12,193,916 B2
(45) Date of Patent: Jan. 14, 2025

(54) DRESSING FOR STUMPS FOLLOWING AMPUTATION

(71) Applicant: SYSTAGENIX WOUND MANAGEMENT, LIMITED, West Sussex (GB)

(72) Inventors: Saul Di Palo, West Sussex (GB); Kyle Turton, West Sussex (GB); Joy Thistlethwaite, West Sussex (GB); Daniel Parker, West Sussex (GB); Clinton Hill, Colne (GB)

(73) Assignee: Systagenix Wound Management, Limited, Bracknell (GB)

( * ) Notice: Subject to any disclaimer, the term of this patent is extended or adjusted under 35 U.S.C. 154(b) by 609 days.

(21) Appl. No.: 17/429,856

(22) PCT Filed: Feb. 13, 2020

(86) PCT No.: PCT/IB2020/051204
§ 371 (c)(1),
(2) Date: Aug. 10, 2021

(87) PCT Pub. No.: WO2020/170088
PCT Pub. Date: Aug. 27, 2020

(65) Prior Publication Data
US 2022/0125645 A1 Apr. 28, 2022

Related U.S. Application Data

(60) Provisional application No. 62/807,558, filed on Feb. 19, 2019.

(51) Int. Cl.
*A61F 13/06* (2006.01)
*A61F 2/78* (2006.01)
(Continued)

(52) U.S. Cl.
CPC ............ *A61F 13/06* (2013.01); *A61F 2/7812* (2013.01); *A61F 13/10* (2013.01); *A61F 13/45* (2013.01);
(Continued)

(58) Field of Classification Search
CPC .......... A61F 13/00; A61F 13/06; A61F 13/08; A61F 13/061; A61F 13/10; A61F 13/101;
(Continued)

(56) References Cited

U.S. PATENT DOCUMENTS 1,355,846 A  10/1920  Rannells
2,547,758 A   4/1951  Keeling
(Continued)

FOREIGN PATENT DOCUMENTS

AU  550575 B2  3/1986
AU  745271 B2  3/2002
(Continued)

OTHER PUBLICATIONS

Louis C. Argenta, MD and Michael J. Morykwas, PHD; Vacuum-Assisted Closure: a New Method for Wound Control and Treatment: Clinical Experience; Annals of Plastic Surgery; vol. 38, No. 6, Jun. 1997; pp. 563-576.
(Continued)

*Primary Examiner* — Keri J Nelson (57) ABSTRACT

An amputation dressing includes a wound contact layer that includes a central panel and three or more petals extending radially from the central panel. The wound contact layer also includes a tube of elastic material twisted to form a point. The point is located substantially centrally along a length of the tube. The tube of elastic material is coupled to the central panel proximate the point. The tube is rolled from a first end of the tube to the point to form a first roll and from a second end of the tube to the point to form a second roll.

20 Claims, 6 Drawing Sheets

(51) Int. Cl.
*A61F 13/10* (2006.01)
*A61F 13/45* (2006.01)
*A61F 13/53* (2006.01)
*A61F 13/56* (2006.01)
*A61F 13/64* (2006.01)
*A61F 13/84* (2006.01)
*A61F 13/00* (2006.01)

(52) U.S. Cl.
CPC .......... *A61F 13/53* (2013.01); *A61F 13/5616* (2013.01); *A61F 13/64* (2013.01); *A61F 13/8405* (2013.01); *A61F 2013/00702* (2013.01); *A61F 2013/4568* (2013.01); *A61F 2013/530481* (2013.01); *A61F 2013/8414* (2013.01)

(58) Field of Classification Search
CPC .......... A61F 13/01–01042; A61F 2013/00361; A61F 2013/00544; A61F 2013/00574–00578; A61F 2013/00655; A61F 2013/00697; A61F 2013/00702; A61F 2013/00089–00106; A61F 2007/0051; A61F 2/50; A61F 2/78; A61F 2/7812; A61F 2002/7818; A61F 2002/7837; A61F 13/104; A61F 2013/00; A61F 2013/702; A61F 2/7825; A61F 2/7837; A61F 2013/00093; A61F 13/105; A61F 13/45; A61F 13/53; A61F 13/5616; A61F 13/64; A61F 13/8405; A61F 2013/4568; A61F 2013/530481; A61F 2013/8414; A41B 13/06; A47D 15/003; B65D 65/06
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,875,758 A * | 3/1959 | Fuzak | A61F 13/105 602/58 |
| 2,910,763 A | 11/1959 | Lauterbach | |
| 2,969,057 A | 1/1961 | Simmons | |
| 3,066,672 A | 12/1962 | Crosby, Jr. et al. | |
| 3,138,156 A * | 6/1964 | Crowell | A61F 13/06 602/61 |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,926,851 A * | 5/1990 | Bulley | D04B 1/18 602/76 |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,499,966 A * | 3/1996 | Bulley | A61F 13/06 602/41 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,316,034 B1 * | 1/2008 | Berry | A41D 13/087 132/73 |
| 10,172,748 B1 | 1/2019 | Wanderman | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0039759 A1 * | 2/2008 | Holm | A61F 13/0226 602/41 |

(56) References Cited

U.S. PATENT DOCUMENTS

| | | | |
|---|---|---|---|
| 2012/0123311 | A1 | 5/2012 | Weidemann-Hendrickson et al. |
| 2012/0179084 | A1 | 7/2012 | Lipshaw et al. |
| 2017/0056250 | A1* | 3/2017 | Donovan ............. A61F 13/108 |
| 2017/0258956 | A1* | 9/2017 | Flach ................. A61F 13/0213 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 054 380 A | 2/1981 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2012/138753 A1 | 10/2012 |
| WO | WO-2018/148086 A1 | 8/2018 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/the British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", the Lancet, Sep. 3, 1983, pp. 532-534.

Chinn, Steven D. et al.: "Closed Wound Suction Drainage", the Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: a New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: a Manual of Its (56) References Cited

OTHER PUBLICATIONS

Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: a Reference Source for Clinicians; Jul. 2007.
International Search Report and Written Opinion on International Patent Application No. PCT/IB2020/051204 dated May 18, 2020 (11 pages).

\* cited by examiner

DRESSING FOR STUMPS FOLLOWING AMPUTATION

CROSS-REFERENCE TO RELATED APPLICATIONS

This application is a US national phase application under 35 USC § 371 of International Application No. PCT/IB2020/051204 filed on Feb. 13, 2020, which claims the benefit of priority to U.S. Provisional Application No. 62/807,558, entitled "DRESSING FOR STUMPS FOLLOWING AMPUTATION" filed on Feb. 19, 2019, which are both hereby incorporated herein by reference in their entireties.

BACKGROUND

In an amputation surgery, a distal portion of a patient's limb or other extremity is removed. The remaining portion of the limb is referred to as an amputation stump. The procedure typically results in one or more surgical wounds (e.g., suture lines) on the stump. The surgical wounds may be positioned at a distal end of the stump, may extend around the stump, may extend along stump from the distal end towards the patient's torso, or some combination thereof. Proper and timely healing of these surgical wounds expedites prosthetic fitting and reduces the risk of complications such as tissue necrosis and re-amputation.

Amputation may also create a risk of stump oedema (i.e., fluid buildup in the stump) as the body adjusts the flow of bodily fluids to adapt to the loss of the portion of the limb, which may lead to further wounds due to deterioration of tissue (e.g., venous ulcer). Applying a compressive force to the stump may resist swelling of the stump and help prevent oedema and related complications.

Patient care may therefore be improved by an amputation dressing that facilitates healing of one or more surgical wounds at an amputation stump while also resisting swelling of the stump.

SUMMARY

One implementation of the present disclosure is an amputation dressing. The amputation dressing includes a wound contact layer that includes a central panel and three or more petals extending radially from the central panel. The wound contact layer also includes a tube of elastic material twisted to form a point. The point is located substantially centrally along a length of the tube. The tube of elastic material is coupled to the central panel proximate the point. The tube is rolled from a first end of the tube to the point to form a first roll and from a second end of the tube to the point to form a second roll.

In some embodiments, the three or more petals comprise six petals spaced equidistantly around the central panel. In some embodiments, the wound contact layer is flower-shaped. In some embodiments, the central panel is positionable abutting a distal end of a stump, the three or more petals are positionable abutting sides of the stump, and an absorbent pad is aligned with the central panel. The first roll is unrollable to cover the wound contact layer, the absorbent pad, and the stump with a first portion of the tube. The second roll is unrollable to cover the first portion of the tube, the wound contact layer, the absorbent pad, and the stump with a second portion of the tube.

In some embodiments, the tube is configured to supply a compressive force that couples the wound contact layer to the stump. In some embodiments, the tube is configured to supply a compressive force that resists swelling of the stump. In some embodiments, the amputation dressing includes a hip attacher configured to couple the tube to a support belt.

In some embodiments, wherein the wound contact layer comprises an anti-microbial material. In some embodiments, the wound contact layer comprises a silicone-coated mesh or film. In some embodiments, the tube includes an elasticated cotton material or a spandex material.

In some embodiments, each petal has a first end positioned proximate the central panel and the first ends combine to form a perimeter of the central panel. In some embodiments, each petal has a second end opposite the first end. The second end having a second width different than a first width of the first end. In some embodiments, each petal is substantially rectangular.

In some embodiments, the dressing includes a pad positioned between the wound contact layer and the tube. In some embodiments, the pad includes a foam material. In some embodiments, the foam material includes a plurality of slits in a mango-cut pattern.

Another implementation of the present disclosure is a method of treating an amputation stump. The method includes positioning a wound contact layer abutting an amputation wound on the amputation stump by aligning a central panel of the wound contact later with a distal end of the amputation stump and positioning three or more petals of the wound contact layer along the amputation stump. The three or more petals extend from the central panel. The method also includes unrolling a first portion of a tube of elastic material over the wound contact layer and the amputation stump and unrolling a second portion of the tube over the first layer, the wound contact layer, and the amputation stump.

In some embodiments, the method includes providing, by the tube, a compressive force that couples the wound contact layer to the amputation stump. In some embodiments, the method includes providing, by the tube, a compressive force that resists swelling of the amputation stump. In some embodiments, the method includes positioning a support belt around a waist of a patient, coupling the support belt to a hip attacher, and coupling the hip attacher to the tube.

In some embodiments, positioning the three or more petals includes substantially covering a circumference of the amputation stump with the three or more petals. In some embodiments, positioning the three or more petals comprises preventing overlap between the three or more petals. In some embodiments, the method includes positioning a pad between the wound contact layer and the tube. In some embodiments, the method includes aligning the pad with the distal end of the amputation stump.

DETAILED DESCRIPTION

Figure 1:
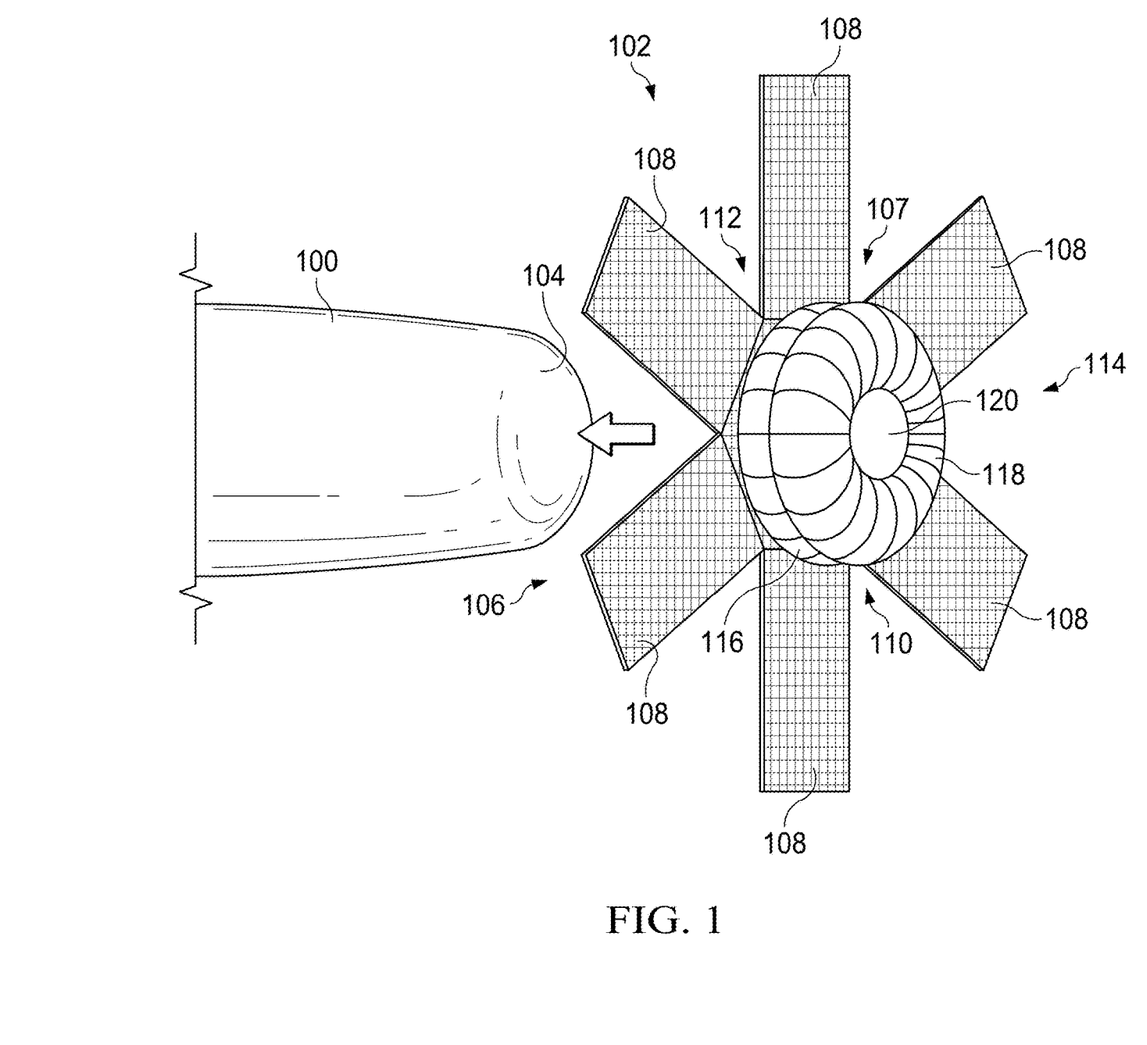
FIG. 1 is a perspective view of an amputation dressing for use in treating an amputation stump, according to an exemplary embodiment.
Figure 2:
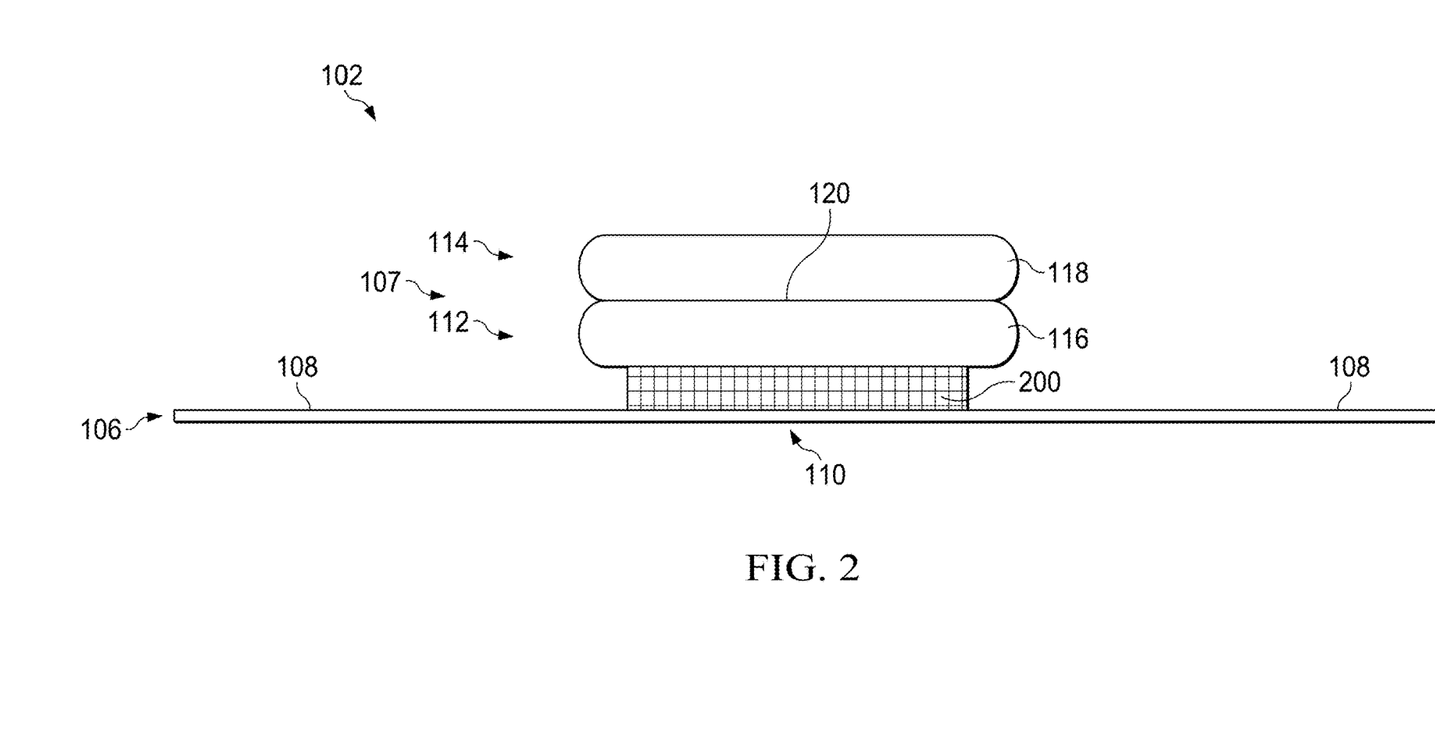
FIG. 2 is a side view of the amputation dressing of FIG. 1, according to an exemplary embodiment.

Referring now to FIGS. 1-2, an amputation dressing 102 is shown, according to exemplary embodiments. FIG. 1 shows a perspective view of an amputation stump 100 with the amputation dressing 102, while FIG. 2 shows a side view of the amputation dressing 102.

The amputation stump 100 is a remaining portion of an extremity of a patient following an amputation procedure to remove a distal portion of that extremity. For example, in some cases the amputation stump 100 may be a remaining portion of an arm or a leg. In some cases, the amputation stump 100 may include a remaining portion of a hand or foot of the patient. The amputation stump 100 includes a distal end 104. Surgical wounds such as suture lines (i.e., areas where surgical incisions are closed with sutures) may be positioned on the distal end 104, extending from the distal end 104 along a length of the stump 100 (i.e., towards the patient's torso), circumferentially around the amputation stump 100, or some combination thereof.

The amputation dressing 102 is configured to facilitate healing of surgical wounds on the amputation stump 100 while also providing compression to the amputation stump 100. By providing wound treatment and compression in a single dressing, the amputation dressing 102 may reduce the time required to dress the amputation stump 100, reduce the bulkiness of the amputation dressing 102 relative to conventional dressing approaches, and reduce or eliminate the risk of pressure injury or other discomfort relative to conventional dressing approaches.

FIGS. 1 and 2 show the amputation dressing 102 in pre-application state, i.e., as the amputation dressing 102 may be configured before application to the amputation stump 100. The amputation dressing 102 includes a wound contact layer 106 coupled to a tube 107. In some embodiments, for example as shown in FIG. 2, the amputation dressing 102 also includes an absorbent pad 200 coupled between the wound contact layer 106 and the tube 107 (e.g., coupled to the wound contact layer 106 and the tube 107). The wound contact layer 106, the tube 107, and/or the absorbent pad 200 may be coupled together by a glue or adhesive (e.g., holt melt adhesive, ethyl vinyl acetate), for example at a glue spot located substantially centrally on the amputation dressing 102.

The wound contact layer 106 is configured to contact one or more surgical wounds on the amputation stump 100. The wound contact layer 106 is made of a material that prevents or substantially prevents adherence to the wound, allowing for gentle and atraumatic removal of the dressing 102 from the wound. For example, the wound contact layer 106 may include silicone, for example a silicone-coated mesh or film. In some embodiments, the wound contact layer 106 may include an antimicrobial material, for example a silicone mesh impregnated with povidone iodine slurry. In various other embodiments, the wound contact layer 106 may be manufactured from silicone gel on a mesh of one or more of cellulose acetate, viscose rayon, polyamide, or polyethylene terephthalate (PET). In some embodiments, the wound contact layer 106 may be coated with petrolatum or lipidocolloid. The wound contact layer 106 may be flexible and extensible to allow the wound contact layer 106 to conform to the contours of the amputation stump 100.

Figure 8:
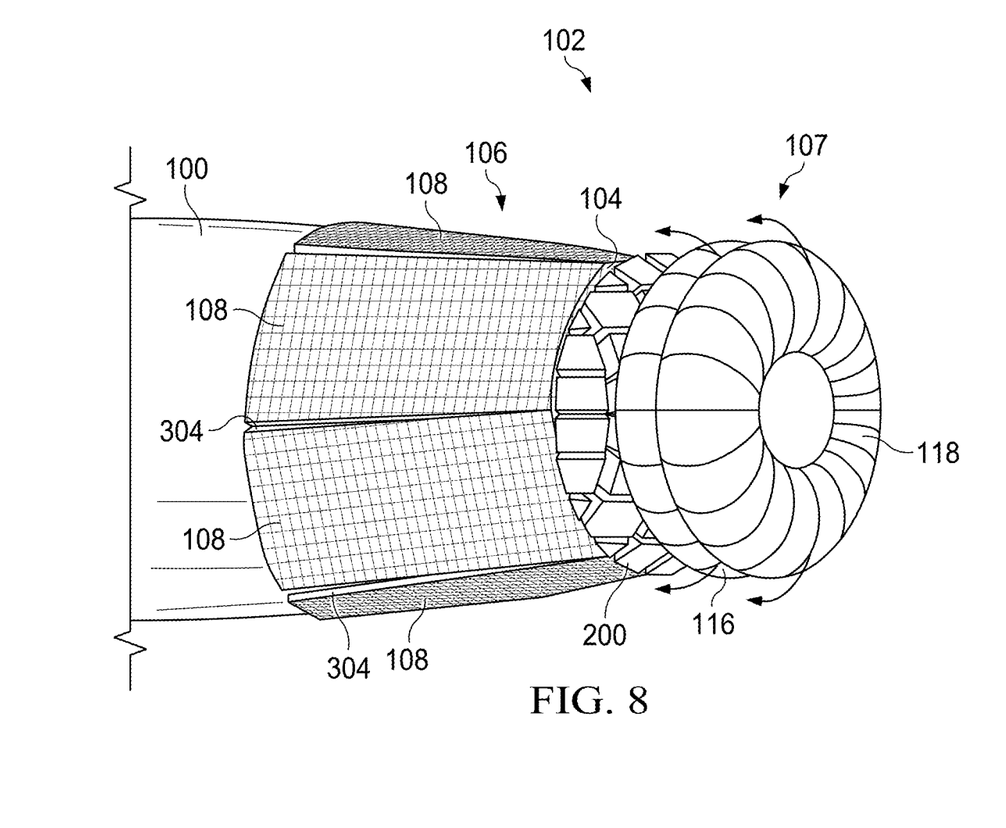
FIG. 8 is a side view of the amputation dressing of FIGS. 1-2 in the process of being applied to an amputation stump, according to an exemplary embodiment.

As shown in FIG. 1, the wound contact layer 106 is substantially "flower-shaped" with multiple panels or wings ("petals") 108 extending from a central panel 110 of the wound contact layer 106. The wound contact layer 106 is shown in detail in FIG. 3 and further described with reference thereto below. The multiple petals 108 are configured to allow the wound contact layer 106 to be positioned around the amputation stump 100, for example to substantially cover a circumference of the amputation stump 100 proximate the distal end 104 of the stump 100. That is, the central panel 110 may be substantially aligned with the distal end 104 of the stump 100 and the petals 108 may be folded (bent, repositioned, etc.) towards the stump 100 and positioned abutting the stump 100 such that the petals 108 align with one another, for example as shown in FIG. 8 and described in detail with reference thereto. The wound contact layer 106 may thereby provide a relatively "non-bulky" and substantially complete coverage of an end portion of the stump 100 without overlap or with minimal overlap between the petals 108 to avoid or minimize pressure points. In some embodiments, the petals may be configured to be cut (e.g., with a scissors) to allow a user to customize a shape of each petal.

The tube 107 is shown to include a first portion 112 and a second portion 114. In the state shown in FIGS. 1 and 2, the first portion 112 is rolled in a first roll 116 and the second portion 114 is rolled in a second roll 118. To create this configuration, the tube 107 is twisted to form a point 120 located substantially centrally along a length of the tube 107. The point 120 separates the first portion 112 from the second portion 114. The first portion 112 is rolled from a first open end of the tube 107 to the point 120 to form the first roll 116 and the second portion 114 is rolled from a second open end of the tube 107 to the point 120 to from the second roll 118. The first portion 112 may be rolled outwardly while the second portion 114 may rolled inwardly, such that the first roll 116 and the second roll 118 can both be unrolled in the same direction (i.e., towards the stump 100), for example to cover an end portion of the stump 100 with both the first portion 112 and the second portion 114. Accordingly, the first roll 116 and the second roll 118 are "unrollable" to cover an end portion of the stump 100. That is, the first portion 112 and the second portion 114 are configured to move from a rolled configuration to an unrolled (elongated tube) configuration.

The tube 107 may be made of an elastic material, for example an elasticated cotton material or a spandex material. In various embodiments, the tube 107 may be manufactured from one or more of woven cotton, PET, or cellulose fibrous material incorporating elastic fibers (e.g., Lycra). For example, the tube 107 may include two-layer short stretch compression stockings. Due to the elasticity of the material of the tube 107, the tube 107 may provide a compressive force when stretched over (i.e., positioned on) an amputation stump 100. This compressive force may act to couple the wound contact layer 106 to the stump 100 (e.g., to substantially hold the dressing 102 in place on the stump 100). The compressive force provided by the tube 107 may also resist and/or substantially prevent swelling of the stump 100, for example to help avoid stump oedema. For example, the tube 107 may provide a therapeutic level of compression (e.g., between approximately 15 mmHg and 40 mmHg) and/or a static stiffness index (e.g., greater than 10 mmHg).

In some embodiments, the tube 107 may include absorbent materials, such as those described with reference to the absorbent pad 200 below. For example, in some embodiments the first portion 112 includes one or more absorbent materials while the second portion 114 includes one or more compressive materials. As another example, the tube 107 may include absorbent fibers of carboxyl methyl cellulose. As another example, the tube 107 may include sodium polyacrylate superabsorbent fibers or particles.

Figure 3:
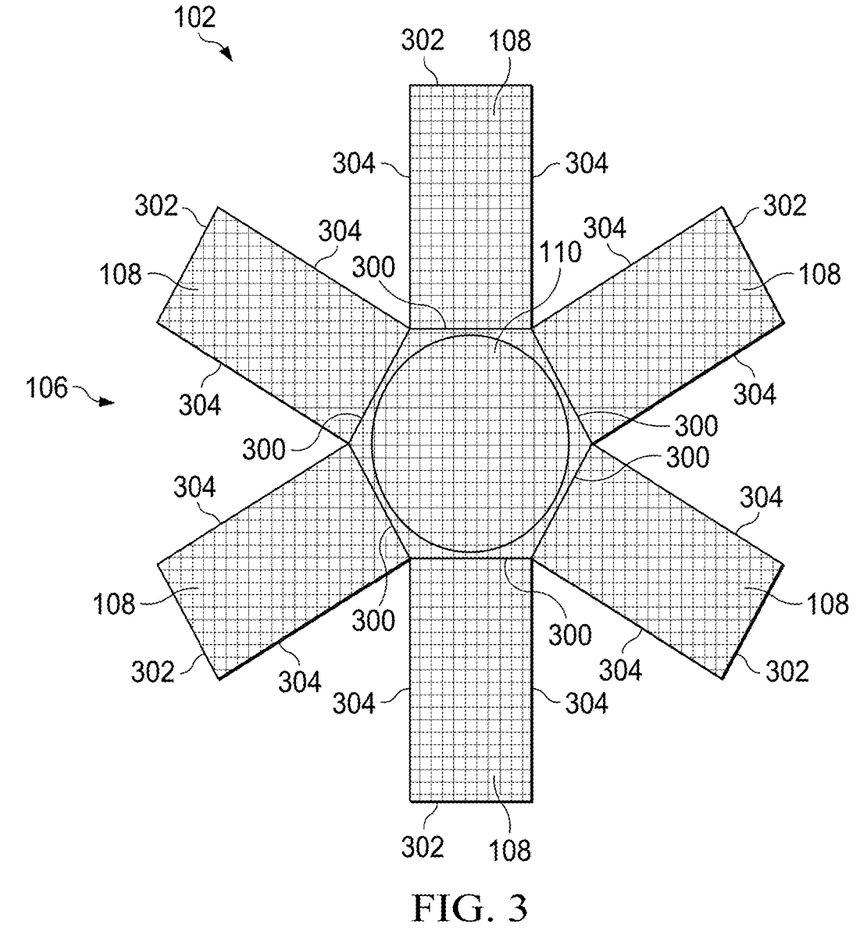
FIG. 3 is a bottom view of a wound contact layer of the amputation dressing of FIGS. 1-2, according to an exemplary embodiment.
Figure 4:
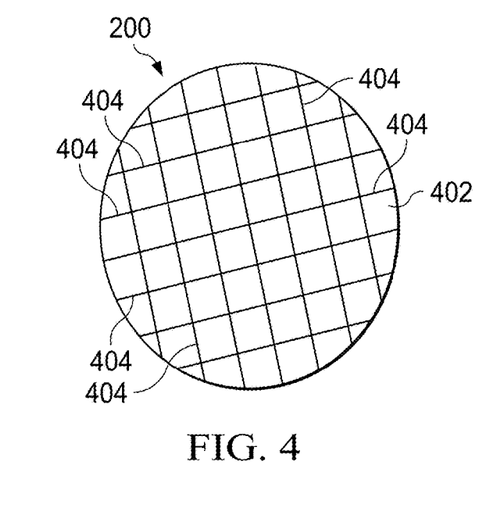
FIG. 4 is a top view of an absorbent pad of the amputation dressing of FIGS. 1-2 according to an exemplary embodiment.
Figure 5:
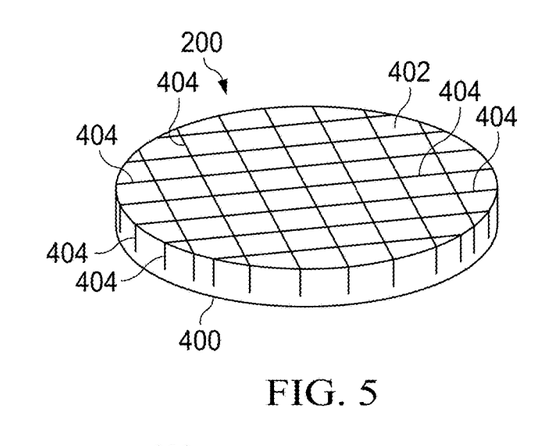
FIG. 5 is a perspective view of the absorbent pad of FIG. 4 in an unbent state, according to an exemplary embodiment.
Figure 6:
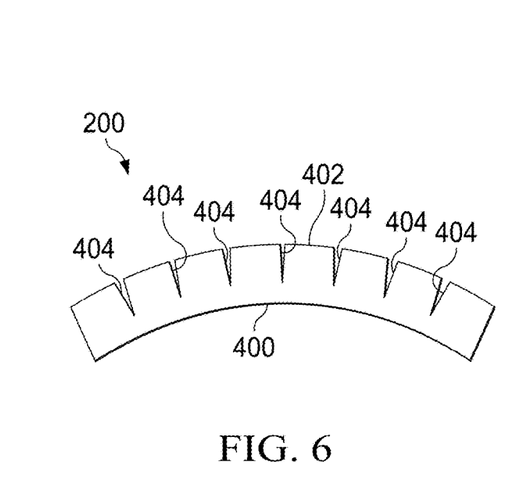
FIG. 6 is a cross-sectional side view of the absorbent pad of FIG. 4 in a bent state, according to an exemplary embodiment.
Figure 7:
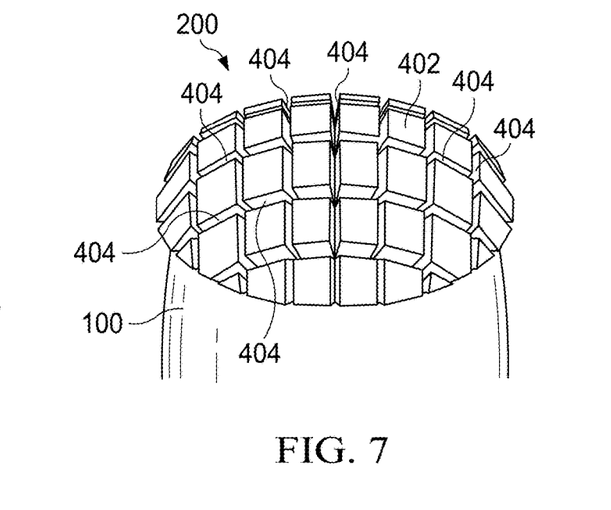
FIG. 7 is a perspective view of the absorbent pad of FIG. 4 applied to an amputation stump, according to an exemplary embodiment.

Referring now to FIG. 3, a bottom view of the dressing 102 is shown, according to an exemplary embodiment. More particularly, FIG. 3 shows a view of the bottom surface of the wound contact layer 106 (i.e., the surface of the wound contact layer 106 configured to contact the stump 100 and/or a surgical wound). The wound contact layer 106 includes a central panel 110 and multiple petals 108 extending radially from the central panel 110. The central panel 110 and the multiple petals 108 may be formed as a single sheet of non-adhesive material or multiple separate sections of material in various embodiments.

In preferred embodiments, the wound contact layer 106 includes three or more petals 108. For example, in the embodiment shown in FIG. 1, the wound contact layer 106 includes six petals 108. Various other numbers of petals 108 are included in various embodiments (e.g., three petals, four petals, five petals, seven petals, eight petals, etc.). The petals 108 may be spaced substantially equidistantly and/or at substantially equal angles around the central panel 110. For example, in an embodiment where the wound contact layer 106 includes six panels, the petals 108 may be arranged to extend radially from the central panel 110 at approximately sixty degree increments. Advantageously, three or more petals provides enhanced coverage and retention/stability of the wound contact layer 106 on the stump 100.

Each petal 108 has a first end 300 adjacent to the central panel 110, a second end 302 opposite the first end 300, and edges 304 that extend from the first end 300 to the second end 302. In the embodiment shown, the first end 300 and the second end 302 are substantially straight and parallel with a substantially equal width, and the edges 304 are substantially straight and have substantially equal lengths. Accordingly, in the embodiment shown, each petal 108 is substantially rectangular. In various other embodiments, various shapes of the petals 108 are possible. For example, in some embodiments one or more of the first ends 300, second ends 302, and edges 304 may be curved or otherwise non-straight. In various embodiments, the width of the first end 300 may different (i.e., wider or narrower) than the width of the second end 302 and/or the edges 304 of a petal 108 may have unequal lengths. For example, the petal 108 may be trapezoidal. As another example, in some embodiments each petal 108 has a mid-region that may be wider or narrower than the first end 300 and/or the second end 302. In some embodiments, each petal 108 has substantially equal dimensions (e.g., the widths of each of the first ends 300 and second ends 302 are substantially equal). In other embodiments, two or more petals 108 have different dimensions.

In the embodiment shown in FIG. 3, the first ends 300 of each petal 108 combine to define a periphery of the central panel 110. The first end 300 of each petal 108 extends between the first ends 300 of two adjacent petals 108. Thus, in the example of FIG. 3 (i.e., where the wound contact layer 106 includes six petals 108) the first ends 300 of the six petals 108 form a hexagon that defines the periphery of the central panel 110. In such embodiments, the sum of the widths of the first ends 300 may be equal to the perimeter of the central panel 110. In various other embodiments, the sum of the widths of the first ends 300 may be less than the perimeter of the central panel 110. Advantageously, petals 108 substantially surround the stump 100 to provide wound coverage with no or substantially no overlap of material (overlap not desirable).

Various dimensions and ratios of dimensions are possible for the central panel 110 and the petals 108. The central panel 110 may be of a suitable size to cover the distal end 104 of an amputation stump 100, while the petals 108 may be of suitable sizes and shapes to cover surgical wounds positioned along the amputation stump 100. Accordingly, the dressing 102 may be manufactured in various sizes and relative dimensions for use with various patients of various sizes, various amputation locations (e.g., above the knee, below the knee, above the elbow, below the elbow), various surgical wounds, etc.

Referring now to FIGS. 4-7, various views of the absorbent pad 200 are shown, according to an exemplary embodiment. The absorbent pad 200 is shown from a top view in FIG. 4, a side view in an unbent state in FIG. 5, a cross-sectional side view in bent state in FIG. 6, and a perspective view as applied to the amputation stump 100 in FIG. 7.

The absorbent pad 200 is configured to absorb wound exudate from one or more surgical wounds on the amputation stump 100 and/or provide cushioning to protect the one or more wounds and provide comfort for the patient. The absorbent pad 200 may be made of a foam, for example a polyurethane foam. In various embodiments, the absorbent pad 200 may be manufactured from one or more of TIELLE Hydropolymer foam by Systagenix or GranuFoam by Acelity. In some embodiments, a foam material of the absorbent pad 200 may be laminated or wrapped in a non-adherent such as ethyl methylacrylate. In some embodiments, the absorbent pad 200 may incorporate an antimicrobial material such as silver fibers or polyhexanide (PHMB). The material of the absorbent pad 200 may be at least partially flexible to facilitate conformance to contours of the amputation stump 100 (e.g., of the distal end 104 of the amputation stump 100).

The absorbent pad 200 includes a bottom surface 400 positioned adjacent the wound contact layer 106 and a top surface 402 positioned opposite the bottom surface 400. The absorbent pad 200 may be substantially circular, for example as shown from the top view of FIG. 4. In some embodiments, the absorbent pad 200 is sized and shaped to substantially match a size and shape of the central panel 110 of the wound contact layer 106. In alternative embodiments, the absorbent pad 200 is substantially flower-shaped to substantially match the size and shape of the wound contact layer 106 including the petals 108. Accordingly, the wound contact layer 106 (e.g., the central panel 110) may separate the absorbent pad 200 from the amputation stump 100 when the dressing 102 is applied to the amputation stump 100.

As shown in FIGS. 4-7, the absorbent pad 200 is cross-hatched with slits or slices 404 that extend partially through a width of the absorbent pad 200 and facilitate bending of the absorbent pad 200. Each slice 404 extends into the absorbent pad 200 from the top surface 402 of the absorbent pad 200 towards the bottom surface 400 without extending through the bottom surface 400. When the absorbent pad 200 is unbent as in FIG. 5, the slices 404 are closed, such that the absorbent pad 200 has a substantially-rectangular cross-section. When the absorbent pad 200 is bent as in FIGS. 6 and 7, for example to conform to the contours of the amputation stump 100, the slices 404 open to create gaps between sections of the top surface 402. The slices 404 thereby allow curvature of the absorbent pad 200 by providing for expansion of the top surface 402.

In the example of FIGS. 4-7, multiples slices 404 are arranged in a pattern that includes a first set of parallel slices 404 and a second set of parallel slices 404. The slices 404 in the first set are perpendicular to the slices 404 in the second set (for example, in the manner of a "mango-cut" pattern or the like). Various other arrangements of slices 404 are possible in various embodiments to allow the absorbent pad 200 to bend in the desired way (e.g., to conform to an amputation stump 100). For example, the slices 404 may be arranged as concentric circles on the absorbent pad 200. It should be understood that various numbers of slices 404 may be included in various embodiments.

Referring now to FIG. 8, a view of the dressing 102 in the process of being applied to the amputation stump 100 is shown, according to an exemplary embodiment. In the state shown in FIG. 8, the wound contact layer 106 has been applied to the amputation stump 100. More particularly, the central panel 110 has been aligned with the distal end 104 of the amputation stump 100 and the petals 108 have been positioned along the amputation stump 100. The edges 304 of adjacent petals 108 are substantially aligned such that no or little gap exists between adjacent petals 108 while substantially avoiding overlap of the petals 108. The wound contact layer 106 thereby encapsulates (covers, contacts, surrounds) an end portion of the stump 100 and/or a circumference around the stump 100.

The absorbent pad 200 is bent to conform to the curvature of the distal end 104 of the amputation stump 100, facilitated by slices 404. The absorbent pad 200 is thereby positioned to absorb wound exudate from surgical wounds at the distal end 104 and provide cushioning at the distal end 104 of the amputation stump 100.

The tube 107 is coupled to the absorbent pad 200. When in the state shown in FIG. 8, the dressing 102 is ready for the first roll 116 and the second roll 118 to be unrolled, as indicated by arrows in FIG. 8. The first roll 116 may be unrolled along the amputation stump 100 to position the first portion 112 of the tube 107 around the amputation stump 100 to cover the wound contact layer 106 and the absorbent pad 200. The second roll 118 may then be unrolled along the amputation stump 100 to position the second portion 114 of the tube 107 around the amputation stump 100 to cover (fully or partially) the first portion 112, the wound contact layer 106, and the absorbent pad 200. When unrolled, the tube 107 may be stretched such that the elastic material of the tube 107 provides a compressive force directed towards the amputation stump 100 (e.g., normal to a surface of the amputation stump 100).

Figure 9:
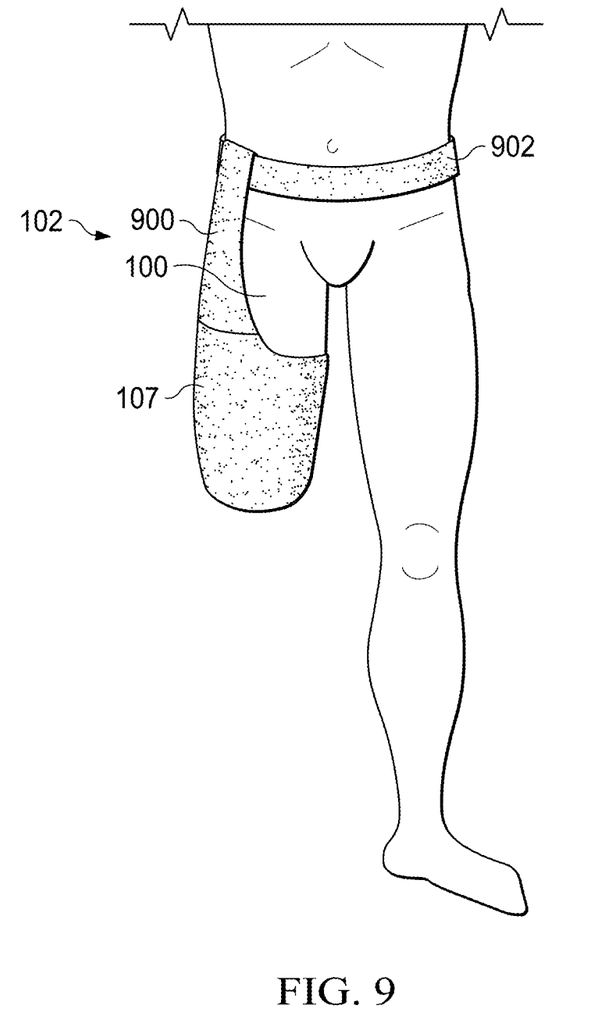
FIG. 9 is an illustration of the amputation dressing of FIGS. 1-2 in use to treat a leg amputation stump of a patient, according to an exemplary embodiment.

Referring now to FIG. 9, an illustration of the amputation dressing 102 in use to treat an amputation stump 100 following a leg amputation is shown, according to an exemplary embodiment. Relative to FIG. 8, the first roll 116 and the second roll 118 have been unrolled to cover the wound contact layer 106 and the absorbent pad 200 and provide compression to the amputation stump 100.

In FIG. 9, the amputation dressing 102 is shown to include a hip attacher 900 that couples the tube 107 to a belt 902. The hip attacher 900 may be made of a similar material as the tube 107 or some other material. The hip attacher 900 may be selectively attached and detached from the tube 107 and/or the belt 902 using snaps, buttons, or some other fastener. In some embodiments, the hip attacher 900 includes a loop configured to receive the belt 902 (i.e., such that the belt 902 may extend through the loop to couple the hip attacher 900 to the loop). In some embodiments, the hip attacher 900 is formed as continuous extension of the tube 107 and/or the belt 902 and/or fixedly coupled (e.g., sewn, glued) to the tube 107 and/or the belt 902. The hip attacher 900 may have an adjustable length.

The belt 902 is configured to hold position around a waist of a patient. As shown in FIG. 9, the hip attacher 900 retains the tube 107 at a substantially constant distance from the belt 902. The belt 902 and hip attacher 900 thereby hold the tube 107 at a substantially constant location relative to the amputation stump 100. In other words, the belt 902 and the hip attacher 900 substantially prevent the tube 107 from slipping off of the amputation stump 100.

While FIG. 9 shows the amputation dressing 102 secured to the waist of a patient, in alternative embodiments the amputation dressing 102 may include a shoulder attachment, for example a shoulder strap coupleable to the tube 107. The shoulder attachment or strap may extend from the amputation dressing 102 applied to an arm of a patient, across the patient's back and/or chest, and around the patient's opposite shoulder. Various configurations of a shoulder attachment are possible.

As detailed in the foregoing description, the amputation dressing 102 thereby provides, in a unified device, coverage of surgical wounds with a wound contact layer 106 that provides adherence-reducing properties, absorption and cushioning with a conformable absorbent pad 200, and compression with a tube 107.

Configuration of Exemplary Embodiments

Other arrangements and combinations of the elements described herein and shown in the Figures are also contemplated by the present disclosure. The construction and arrangement of the systems and apparatuses as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. Other substitutions, modifications, changes, and omissions can be made in the design, operating conditions and arrangement of the exemplary embodiments without departing from the scope of the present disclosure.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

What is claimed is:

1. An amputation dressing, comprising:
   a wound contact layer comprising:
      a central panel; and
      three or more petals extending radially from the central panel, each of the three or more petals including an edge, wherein the edge of each of the three or more petals is configured to be aligned with the edge of an adjacent petal of the three or more petals along at least a portion of a stump;
   a tube comprising an elastic material twisted to form a point, the point located along a length of the tube, the tube coupled to the central panel proximate to the point;
   wherein the tube is rolled from a first end of the tube to the point to form a first roll and from a second end of the tube to the point to form a second roll.

2. The amputation dressing of claim 1, wherein the three or more petals comprise six petals spaced equidistantly around the central panel.

3. The amputation dressing of claim 1, wherein:
   the central panel is configured to be positioned abutting a distal end of the stump;
   the three or more petals are configured to be positioned abutting sides of the stump;
   an absorbent pad is configured to be aligned with the central panel;
   the first roll is configured to be unrolled to cover the wound contact layer and the stump with a first portion of the tube;
   the second roll is configured to be unrolled to cover the first portion of the tube, the wound contact layer, and the stump with a second portion of the tube.

4. The amputation dressing of claim 3, wherein the elastic material of the tube is configured to couple the wound contact layer to the stump.

5. The amputation dressing of claim 4, wherein the elastic material of the tube is configured to resist swelling of the stump.

6. The amputation dressing of claim 1, further comprising a hip attacher configured to couple the tube to a support belt.

7. The amputation dressing of claim 1, wherein the wound contact layer comprises an anti-microbial material.

8. The amputation dressing of claim 1, wherein the wound contact layer comprises a silicone-coated mesh or film.

9. The amputation dressing of claim 1, wherein the tube comprises an elasticated cotton material or a spandex material.

10. The amputation dressing of claim 9, wherein each of the three or more petals have a second end opposite the first end, the second end having a second width different than a first width of the first end.

11. The amputation dressing of claim 1, wherein each of the three or more petals are rectangular.

12. The amputation dressing of claim 1, comprising a pad positioned between the wound contact layer and the tube.

13. The amputation dressing of claim 12, wherein the pad comprises a foam material having a plurality of slits in a mango-cut pattern.

14. A method of treating an amputation stump, comprising:
   positioning a wound contact layer abutting an amputation wound on the amputation stump by:
      aligning a central panel of the wound contact layer with a distal end of the amputation stump;
      positioning three or more petals of the wound contact layer along the amputation stump, the three or more petals extending from the central panel, each of the three or more petals including an edge, wherein the edge of each of the three or more petals is aligned with the edge of an adjacent petal of the three or more petals along at least a portion of the amputation stump; and
   unrolling a first portion of a tube comprising an elastic material over the wound contact layer and the amputation stump; and
   unrolling a second portion of the tube over a first layer of the first portion of the tube, the wound contact layer, and the amputation stump.

15. The method of claim 14, comprising providing, by the tube, a compressive force that couples the wound contact layer to the amputation stump.

16. The method of claim 14, comprising providing, by the tube, a compressive force that resists swelling of the amputation stump.

17. The method of claim 14, comprising:
   positioning a support belt around a waist of a patient;
   coupling the support belt to a hip attacher; and
   coupling the hip attacher to the tube.

18. The method of claim 14, wherein positioning the three or more petals comprises covering at least a portion of a circumference of the amputation stump with the three or more petals.

19. The method of claim 14, wherein positioning the three or more petals comprises preventing overlap between the three or more petals.

20. The method of claim 14, further comprising positioning a pad between the wound contact layer and the tube and aligning the pad with the distal end of the amputation stump.

* * * * *